United States Patent [19]
Lichtman

[11] Patent Number: 5,611,813
[45] Date of Patent: Mar. 18, 1997

[54] SURGICAL INSTRUMENT

[75] Inventor: Philip R. Lichtman, Newton, Mass.

[73] Assignee: Microsurge, Inc., Needham, Mass.

[21] Appl. No.: 431,023

[22] Filed: Apr. 28, 1995

Related U.S. Application Data

[60] Division of Ser. No. 26,489, Mar. 4, 1993, abandoned, which is a continuation-in-part of Ser. No. 869,535, Apr. 15, 1992, Pat. No. 5,318,589.

[51] Int. Cl.$^6$ .................................................... A61B 17/32
[52] U.S. Cl. ........................ 606/205; 606/174; 128/751
[58] Field of Search ................................ 606/51, 52, 174, 606/205–211; 604/22; 128/750–755

[56] References Cited

U.S. PATENT DOCUMENTS 3,404,677  10/1968  Springer .
4,427,014  1/1984   Bel et al. .
4,896,678  1/1990   Ogawa .

Primary Examiner—Michael Powell Buiz
Assistant Examiner—William Lewis
Attorney, Agent, or Firm—Pandiscio & Pandiscio

[57] ABSTRACT

A surgical instrument is provided of the type having first and second telescoping shafts, a jaw assembly comprising two jaws carried by the front end of the first shaft, and a novel handle mechanism, and connecting member for connecting the rear ends of the two shafts to the novel handle mechanism, so that manipulation of the handle mechanism by the surgeon will cause relative reciprocal axial motion of the two shafts, thereby resulting in opening and closing of the jaws. In a preferred embodiment, the novel handle mechanism comprises a first fixed handle member, a second movable handle member, gear member connecting the two handle members so that when the handles are moved relative to one another in a first direction, the jaws will be squeezed into clamping relation with tissue by the collet-like action of the second shaft moving in a first direction relative to the second shaft, and spring member for urging the second shaft to move in a direction to open the jaws. The instrument may include a device member for conducting electrosurgery, releasable locking member for locking the two handle members so that the jaws are releasably locked in gripping engagement with tissue, a reversing gear for reversing the effect of movement of the two handle members on the two jaws so as to accommodate jaw mechanisms of different designs, and/or device for conducting cleaning of the instrument or irrigation of the surgical site.

28 Claims, 10 Drawing Sheets

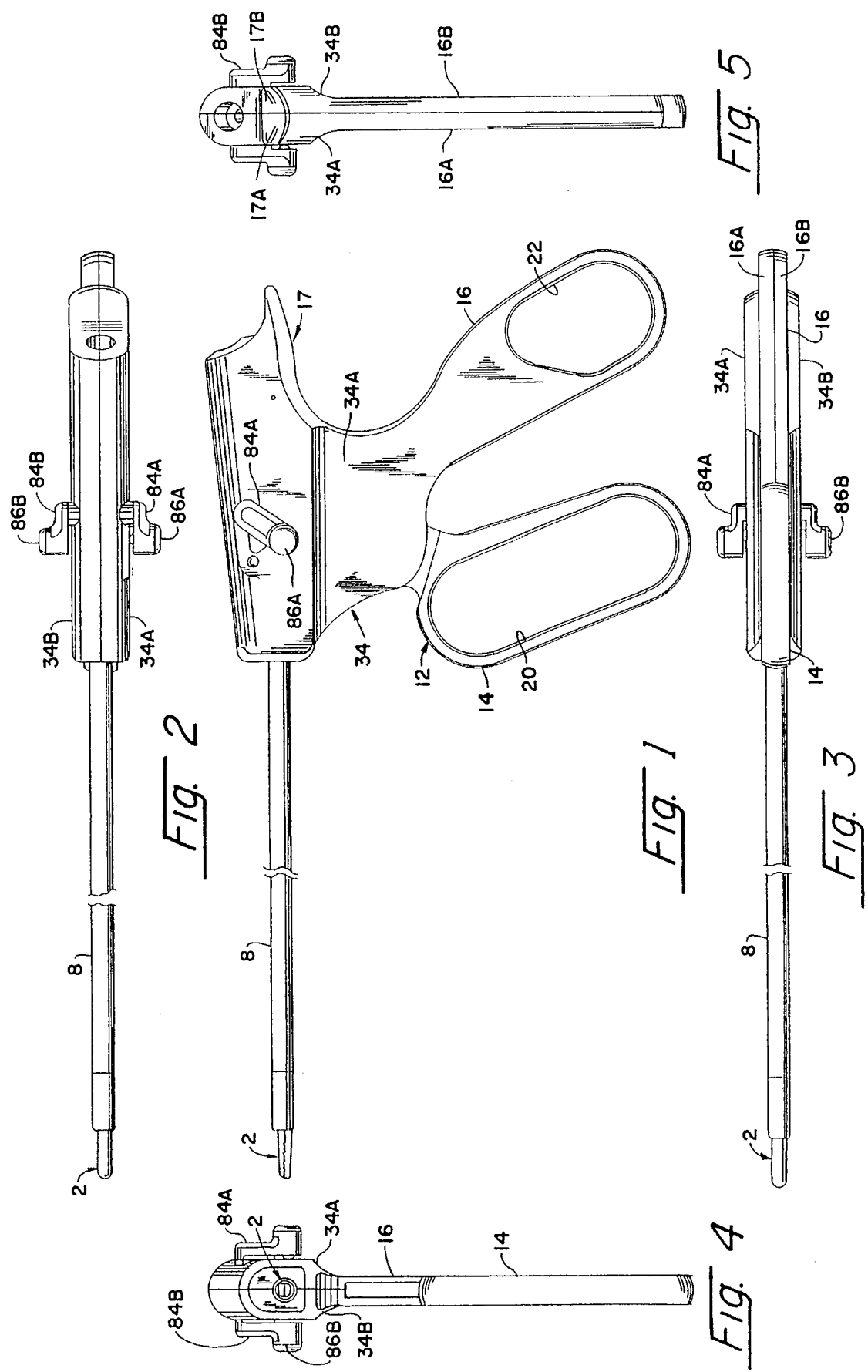

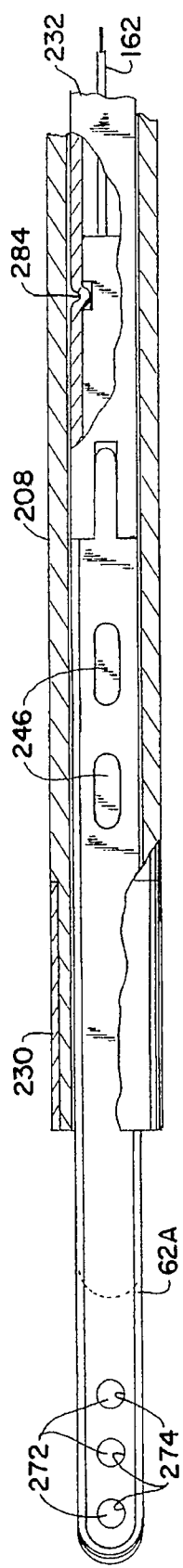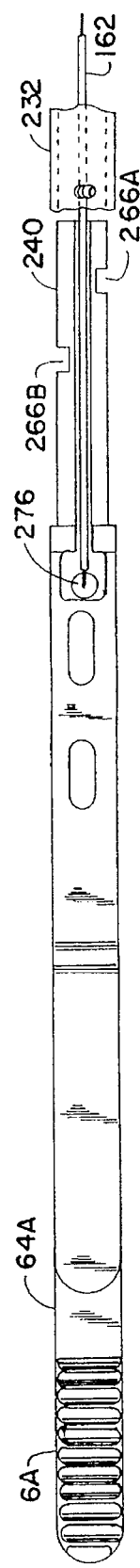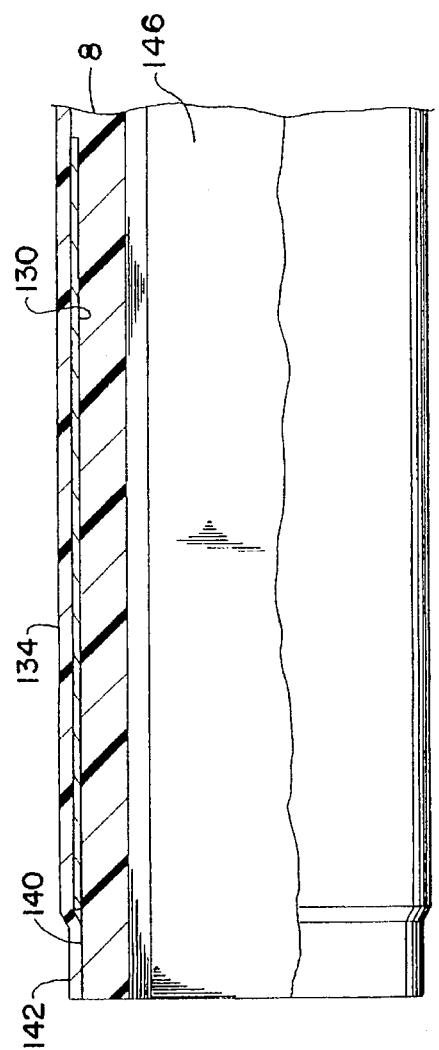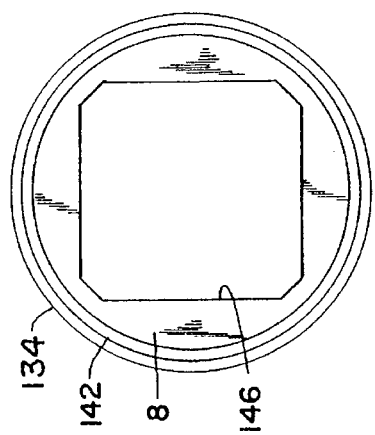

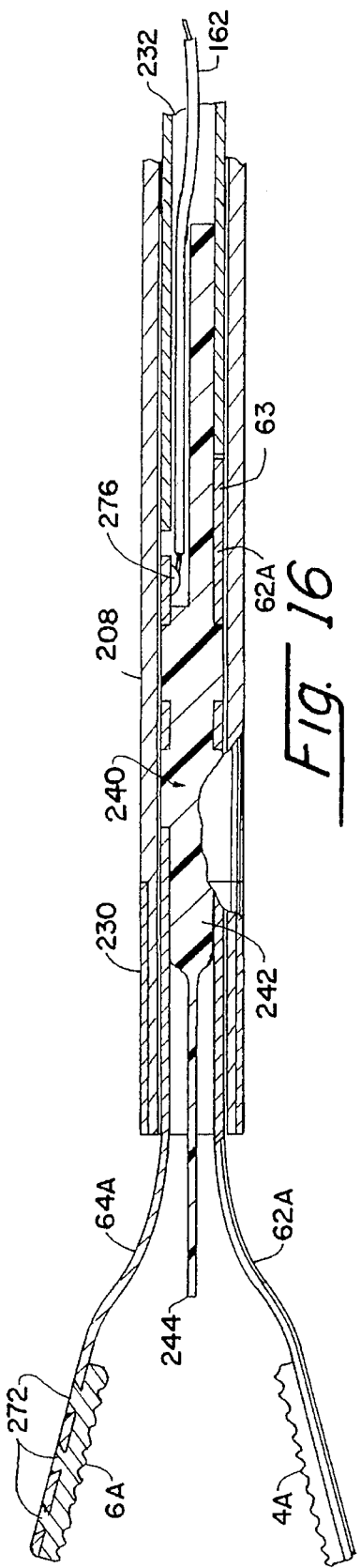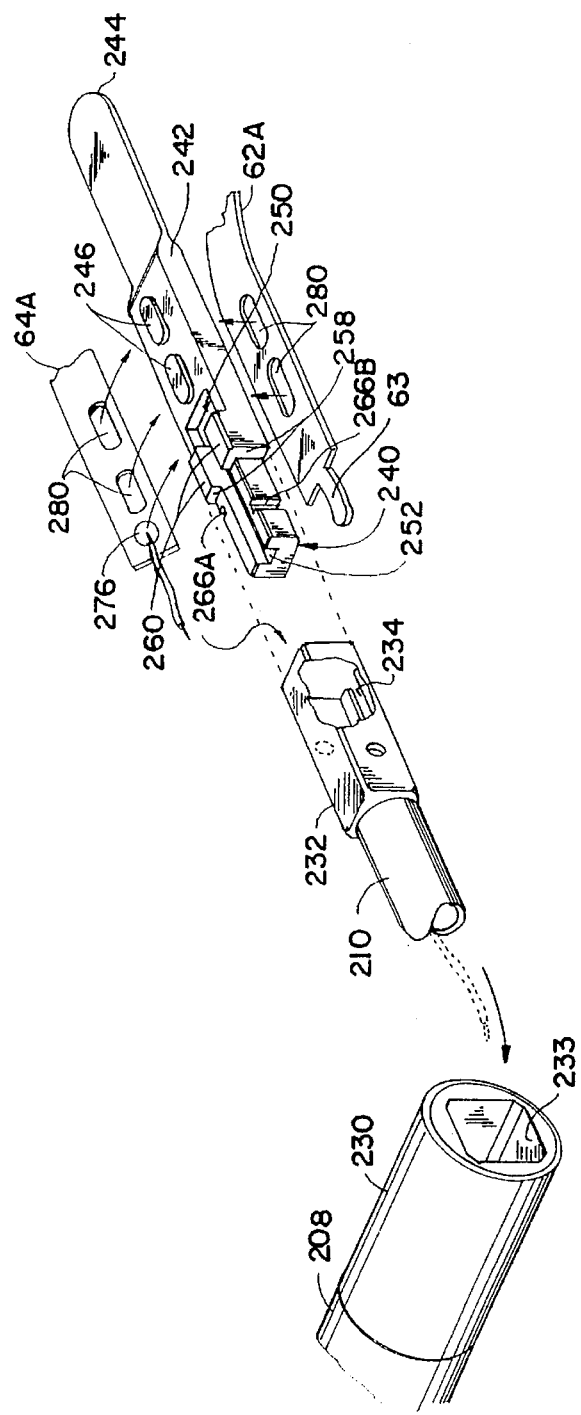

SURGICAL INSTRUMENT

This is a division of U.S. application Ser. No. 08/026,489 filed Mar. 4, 1993, now abandoned for "Surgical Instrument," which is a continuation-in-part of U.S. application Ser. No. 07/869,535, filed Apr. 15, 1992, now U.S. Pat. No. 5,318,589, issued Jun. 7, 1994.

This invention relates to surgical instruments for manipulating tissue and other objects and more particularly to improvements in instruments such as graspers and forceps for facilitating freedom of the hands of the surgeon and also for conducting electrosurgery.

My prior application Ser. No. 07/869,535 relates to an improved grasper-type instrument which is characterized by a unitary piece jaw comprising two jaws, a rear section, and two intermediate leaf spring sections each connecting a different jaw to the rear section of the jaw piece, with the jaw piece being affixed to one end of a first shaft that is in telescoping arrangement with a second shaft, whereby when the second shaft is caused to translate toward the distal end of the first shaft, the second shaft will slide over the jaws and cause them to close toward one another.

BACKGROUND OF THE INVENTION

As used herein, the term "tissue and other objects" means and includes human or animal organs, blood vessels, bones, tendons, ligaments and connective or covering tissue or skin as examples of tissue, and sutures, needles, staples, implants, surgical devices and foreign bodies such as shrapnel or bullet fragments, as examples of "other objects". Also as used herein, the term "electrosurgery" means and includes electro-cauterization and electro-cutting of tissue.

During surgical operations, it is often necessary for the surgeon to be able to manipulate blood vessels, ligaments or other tissue precisely, particularly when the surgeon is relatively remote from the surgical site, as is the case in performing endoscopic procedures. As used herein, the term "manipulate" includes such functions as grasping, clamping, cutting and suturing. Among the instruments that are used for manipulating as herein defined are graspers, forceps, clamps, dissectors, incisors, scissors, cauterizers, needle holders, etc. Often the manipulating is achieved by means of an instrument having a two-part handle mechanism, a tissue-interacting head comprising two or more tissue-interacting members (e.g., jaws), and a head supporting and operating means coupling the handle mechanism and the tissue-interacting head for causing the tissue-interacting members to be moved into and out of a closed relation with one another by the surgeon's manipulation of the handle mechanism.

In a typical prior art instrument, the head supporting and operating means comprises a first shaft fixed to one part of the handle mechanism, a second operating shaft disposed in coaxial and telescopic relation with the first shaft, and means connecting the second shaft to the other part of the handle mechanism, so that telescoping movement of one shaft relative to the other shaft is produced when the two parts of the handle mechanism are moved toward and away from one another, with the two shafts coacting to cause opening and closing of the tissue-interacting members according to the direction of telescoping movement of one shaft relative to the other. In one typical grasper construction, two jaws are pivotally attached to one end of an outer hollow shaft, and a linkage operated by an inner shaft causes the jaws to be opened or closed in response to telescoping movement of the inner and outer shafts. In another grasper construction, the jaw mechanism comprises a pair of spring-like jaws carried entirely by the inner shaft, with the outer shaft acting as a collar to provide a collet-like action whereby (a) the jaws are forced together when the inner and outer shafts undergo relative telescoping movement in one direction and (b) the jaws are released so as to allow them to open when the telescoping movement is in the reverse direction.

A number of surgical instruments designed to grasp or otherwise manipulate tissue, are commonly provided with some form of locking means for locking the jaws in a gripping position, so that during a surgical procedure, the surgeon may let go of the instrument to attend to some other task in the same surgical procedure without fear of the instrument failing to retain its grip. Various forms of locking means have been used in prior surgical instruments, e.g., interlocking ratchet teeth on confronting handles of a two-part handle mechanism of the type where each handle has a hole for accommodating a finger or thumb of the surgeon. Other types of locking means may require or use a lever or a button element for engaging or disengaging the locking means.

Many surgical instruments utilize a scissors-like handle design having two pivotally connected handle members with finger loops for enabling the surgeon to grip and manipulate the handle members. Other surgical instruments have so-called "pistol-grip" handle mechanisms, which offer certain advantages over scissors-type handle designs.

Prior surgical instruments, particularly those of the grasper or dissector type, frequently employ electrical elements for electrifying selected portions of the distal end of the instrument for electrosurgery purposes. Some prior art instruments are necessarily limited to monopolar electrification where the patient's body is electrically grounded, while others are adapted for bipolar electrification.

Prior surgical instruments of the foregoing type have been characterized by one or more limitations and disadvantages, such as the possibility of the patient being traumatized as a result of the surgeon exerting excessive manual strength on the handles of the instrument, causing tissue to be grasped too tightly. Another disadvantage is that some prior locking mechanisms which require the surgeon to operate a separate control such as a lever or button to engage or disengage the locking mechanism, are so constructed that the location or construction of such lever or button may render the instrument less comfortable or easy to hold and/or maneuver. Still other forms of prior instruments of the type to which the invention relates suffer from the fact that they are not well adapted for electrosurgery or cannot be adapted for both monopolar and bipolar electrosurgery. Other instruments have the disadvantage that they have handle designs which are uncomfortable to hold or which are difficult to hold steady when the handle mechanism is being actuated.

Prior handle mechanism designs also suffer from the fact that they are not suited for multi-purpose instruments.

SUMMARY OF THE INVENTION

A primary object of the invention is to provide an instrument which improves upon the instruments disclosed in my prior copending application Ser. No. 07/869,535. Now U.S. Pat. No. 5,318,589.

Another primary object is to provide a novel handle mechanism for a variety of surgical instruments.

Another object of the invention is to provide an instrument which combines grasping jaws and an improved handle mechanism comprising means remote from the jaws for causing the jaws to open and close in a predetermined manner.

Still another object of the invention is to provide an improved surgical instrument for grasping or otherwise manipulating tissue which has a novel handle mechanism that can be held and operated in either a scissors or a pistol-grip manner.

Still another object is to improve upon surgical instruments of the type comprising a pair of movable jaws or blades and a pair of telescoping shafts for supporting and operating the jaws by providing a handle arrangement that can be adapted to provide four different telescoping motions.

A further object of the invention is to improve on surgical instruments of the type characterized by two or more movable interacting elements (e.g., jaws) and means including a handle assembly for moving those elements into and out of interacting relation with tissue or other objects, by providing a novel handle mechanism comprising first and second handle members and an automatic locking means whereby when the handle members have been moved to place the interacting elements in a predetermined tissue (or object)-engaging position, the two handle members and hence the interacting elements are automatically locked against reverse movement, so that if the surgeon removes his hand from the instrument, the interacting elements will remain in engagement with the tissue or other object.

Still another object is to provide an improved surgical instrument of the type having a pair of jaws, a handle mechanism comprising first and second handle members movable relative to one another, and a jaw supporting and operating means connecting the jaws to the handle mechanism whereby the jaws are opened and closed by relative movement of the handle members, characterized in that the handle mechanism comprises means for incrementally locking the jaws in grasping relation with tissue or other objects as the handle members are moved relative to one another, and also means for electrifying the tool for electrosurgery purposes.

A further object is to provide a multipurpose surgical instrument and/or an instrument that may be adapted for monopolar or bipolar electrosurgery purposes.

The foregoing and other objects and advantages are achieved by an improved surgical instrument that essentially is characterized by first and second shafts disposed in axial telescoping relation with one another, a jaw assembly or head at the distal (front) end of the first shaft, with the proximal (rear) end of the first shaft being affixed to a novel handle mechanism that is also coupled to the second shaft, so that manipulation of the handle mechanism by the surgeon will cause the second shaft to reciprocate axially relative to the first shaft, thereby resulting in opening and closing of the jaw assembly. The jaw assembly preferably comprises two diametrically opposed jaws capable of being moved toward and away from one another, but may comprise more than two jaws capable of similar movement. The handle mechanism comprises (1) first and second handle members, the first handle member being fixed to the proximal end of the first shaft, and the second handle member being pivotally mounted to the first handle, (2) a rack and gear means connecting the second handle member and the second shaft so that when the handles are moved relative to one another in a first direction, the jaws attached to the first shaft will be squeezed into clamping relation with tissue or other matter in a collet-like manner by the action of the second shaft moving in a first direction relative to the first shaft, and (3) means for urging the second shaft to move in a direction to return the jaws to open position. The handle mechanism is arranged so that it may be held and operated in either a pistol-grip or a scissors-type mode. In a preferred embodiment, the novel handle mechanism is characterized by a ratchet-type locking mechanism for automatically locking the two handle members in gripping engagement with tissue or other objects (even if the surgeon accidentally or deliberately loses control of the instrument), and means for releasing the locking mechanism so that the two handle members are free to open and release the grasped tissue or other object.

In still another embodiment, the instrument is provided with a reversing gear for reversing the effect of movement of the two handle members on the two jaws.

Other features and advantages of the invention are illustrated in the accompanying drawings and/or described or rendered obvious by the following specific description of preferred and alternative embodiments of the invention.

BRIEF DESCRIPTION OF THE DRAWINGS

FIG. 1 is a fragmentary left-hand side view in elevation of a grasper constituting a preferred embodiment of the invention, showing the jaws completely closed and correspondingly the handle members squeezed together as far as possible;

FIG. 2 is a plan view of the instrument of FIG. 1;

FIG. 3 is a bottom view of the instrument of FIG. 1;

FIGS. 4 and 5 are front and rear elevational views of the same instrument;

FIG. 13 is a longitudinal sectional view in side elevation of a modification of the tool incorporating electrical insulation means for preventing capacitively-coupled electrical energy from being transmitted to the patient;

FIG. 14 is a front view of the structure shown in FIG. 13;

FIG. 16 is an enlarged fragmentary sectional view in side elevation showing the front end of the bipolar cauterization instrument of FIG. 15;

FIG. 17 is a fragmentary plan view of one of the jaw members of the embodiment of FIGS. 15 and 16;

FIG. 18 is a bottom view of the other jaw member of FIG. 16;

FIG. 19 is an exploded view illustrating components of the front end of the same instrument;

In the drawings, like numerals identify like elements of construction.

PREFERRED EMBODIMENT OF THE INVENTION

As noted hereinabove, surgical instruments employing movable jaws and mechanisms for moving the jaws typically involve coaxial telescoping elements in the form of a hollow outer shaft and an inner shaft which may be hollow or take the form of a solid rod. Additionally, the various jaw mechanisms typically used in surgical instruments require or use one of two different combinations of motion for opening and closing the tissue-engaging elements or jaws. Those two combinations of motion are as follows: (1) reciprocating the outer shaft relative to the inner shaft, with the latter being fixed against movement relative to the handle mechanism; and (2) reciprocating the inner shaft relative to the outer shaft, with the latter being fixed against movement relative to the handle mechanism. It is also recognized as possible to design a system in which both the outer and inner shafts may move at the same time. However, since it is the relative motion between the inner and outer shafts that is material, any combination resulting in a differential movement, either additive or subtractive, would provide a net effect that is not qualitatively different than the two reciprocal motions described above.

The present invention is concerned with providing surgical instruments of the type described with handle mechanisms designed specifically to have any one of four reciprocal motions as follows: (1) the inner shaft is fixed to the handle unit and the outer shaft is coupled to a movable driver means on the handle unit, with closing operation of the handle unit involving forward telescoping movement of the outer shaft by the driver means; (2) the inner shaft is fixed to the handle unit and the driver means includes a reversing gear mechanism coupled to the outer shaft, whereby closing operation of the handle unit is characterized by rearward telescoping movement of the outer shaft; (3) the outer shaft is fixed to the handle unit, and the inner shaft is coupled to a movable driver means on the handle unit, with closing operation of the handle unit involving forward telescoping movement of the inner shaft by the driver means; and (4) the outer shaft is fixed to the handle unit, and the driver means in the handle unit includes a reversing-gear mechanism, whereby closing operation of the handle unit is characterized by rearward telescoping movement of the inner shaft relative to the outer shaft.

Figure 7:
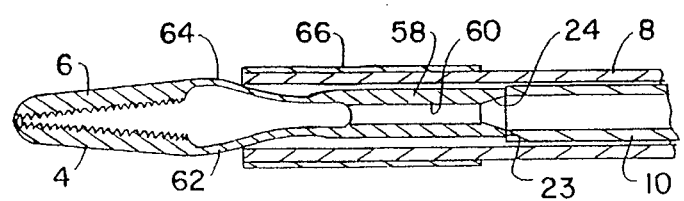
FIG. 7 is a longitudinal sectional view in side elevation of the tip (or jaw end) portion of the same tool, except that the jaws are shown incompletely closed, contact between them having just been initiated at the remote outermost end of the jaws.

Notwithstanding the fact that the mechanical arrangement presently preferred in the industry for graspers and the like is to have a tool wherein the outer shaft is fixed to the handle mechanism and the inner shaft moves telescopically relative to the outer shaft, the preferred embodiment of the invention involves a handle mechanism that is capable of moving the outer shaft forwardly and rearwardly relative to the inner shaft to effect closing and opening respectively of the jaws. However, in contemplation of providing multipurpose instruments, modifications of the invention are disclosed which including fixing the outer shaft and moving the inner shaft relative to the outer shaft, and/or providing a reversing gear whereby movement of the handle members will provide opposite relative movement of the inner and outer shafts. The latter modification is significant in that many types of jaw mechanisms require or may be improved by utilizing a reverse kinematic relationship of the handle mechanism and the members coupled thereto. Referring now to FIGS. 1–9, the instrument shown therein includes unitary jaw piece 2 divided at its front end into two or more jaws 4 and 6, an outer hollow shaft 8, inside of which resides an inner shaft 10 (FIG. 7), a handle assembly identified generally by numeral 12, and a stationary housing 34. Inner shaft 10 may be a solid rod, but preferably it is a hollow shaft as shown in FIG. 7. Handle assembly 12 includes a stationary handle member 16 and a movable handle member 14 that is rotatable with respect to stationary handle member 16 about a pivot pin or rod 18 (FIG. 9). Handle member 16 is formed integral with and forms an extension of housing 34. Operation of the handle members is facilitated by finger loops 20 and 22 on handle members 14 and 16.

Figure 8:
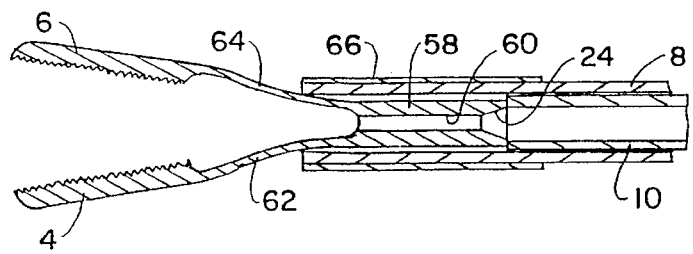
FIG. 8 is a longitudinal sectional view in side elevation, similar to FIG. 1, except that the jaws are shown fully open.
Figure 6:
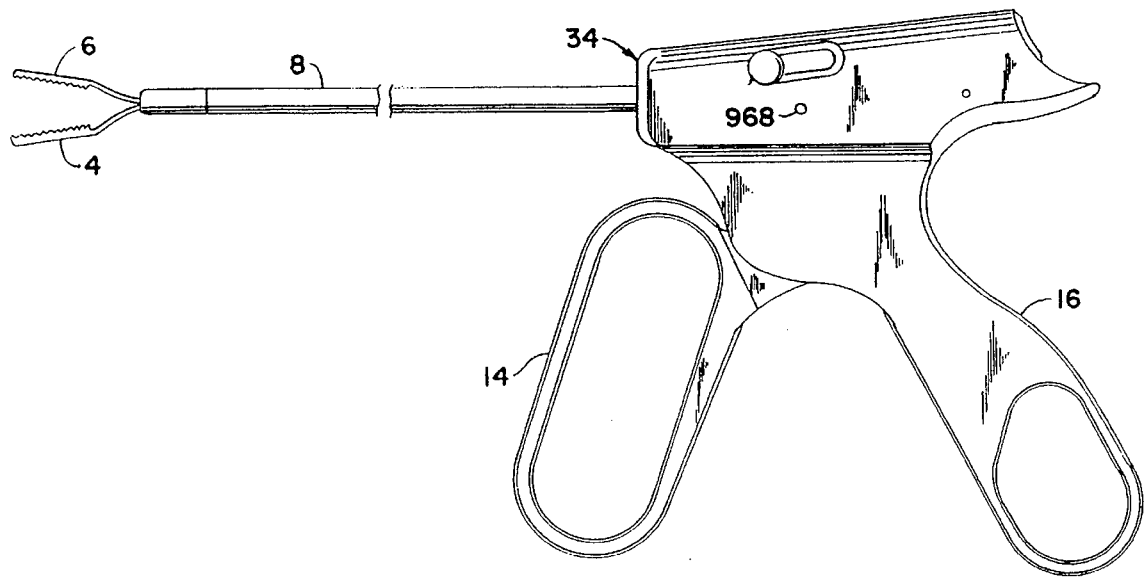
FIG. 6 is a view like FIG. 1 showing the jaws in fully open position.
Figure 9:
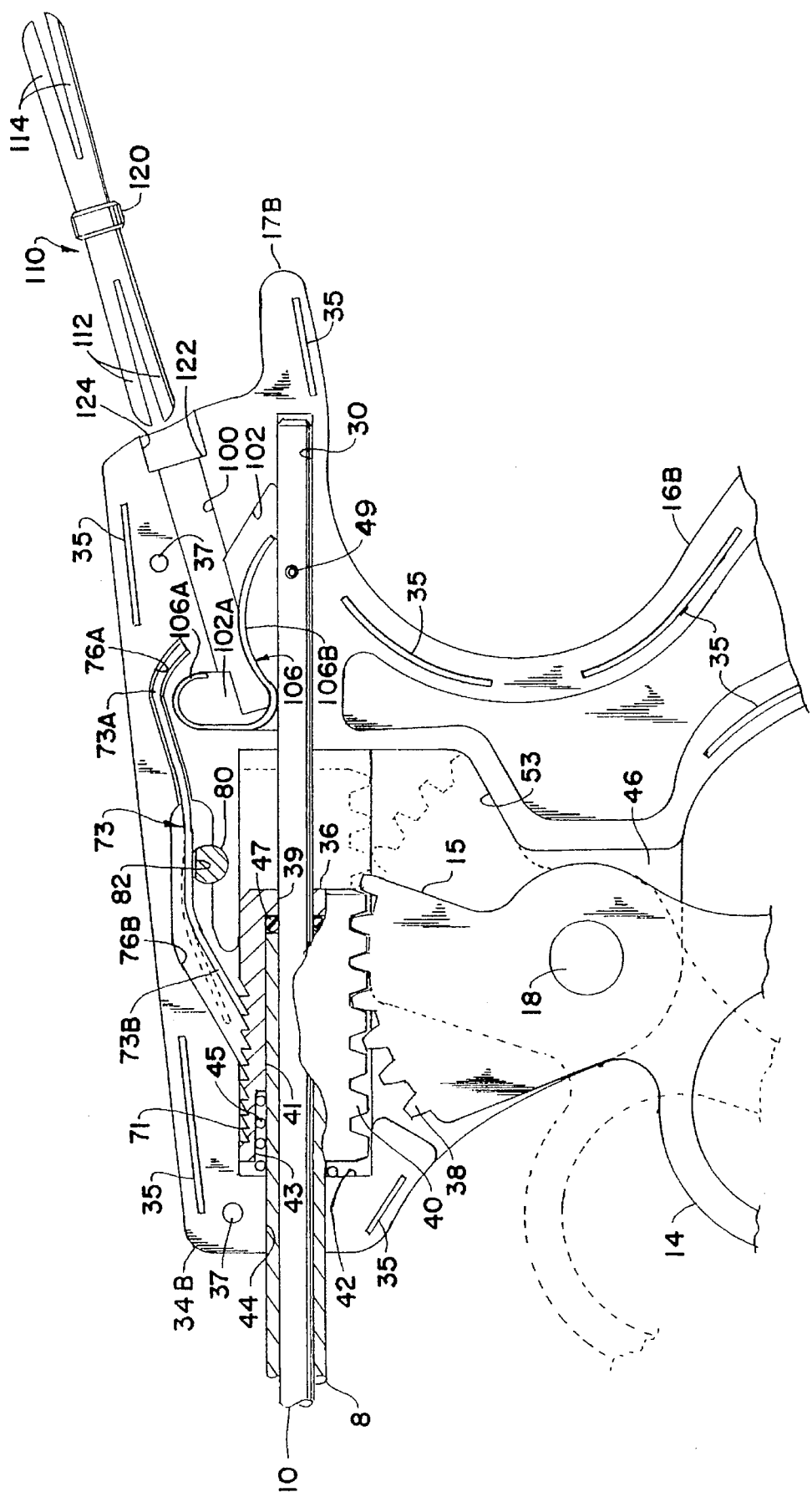
FIG. 9 is a partially exploded, fragmentary sectional view in side elevation illustrating the ratchet-type locking mechanism provided according to the present invention, and also showing the connector used to electrify the instrument.

As seen best in FIGS. 7–9, jaw piece 2 is affixed to and spaced from housing 34 by inner shaft 10, such as by welding the rear end face 23 of jaw piece 2 to the front end of shaft 10.

Outer shaft 8, which coaxially surrounds and is free to slide axially relative to inner tube 10, is rigidly joined to a gear rack tube or sleeve 36, e.g., by a press fit, a cement, welding or a pin. Outer shaft 8 and gear rack tube 36 slide freely relative to inner shaft 10. Gear rack sleeve 36 is formed with a rear bore 39 sized to make a close sliding fit with inner shaft 10, a first counterbore 41 sized to snugly receive the proximal (rear) end of outer shaft 8, and a second counterbore 43 that receives a compression spring 45 that surrounds outer shaft 8. The forward end of spring 45 engages the adjacent forward end wall of gear rack tube chamber 42 (hereinafter described) and thereby acts to urge gear sleeve 36 to move rearwardly in that chamber. Tube 36 is formed with a rack or set of gear teeth 40 spaced along its length in a straight line. An O ring 47 is disposed in gear rack tube 36 between its inner end wall and the inner end of outer shaft 8. The O-ring surrounds and grips inner shaft 10 and acts as a sliding seal to prevent body fluids from travelling from the jaw piece 2 between shafts 8 and 10 into the handle housing 34, from which the fluids could escape to the surrounding environment.

Housing 34 is formed in two mating parts 34A and 34B (FIG. 2, 3, 5 and 9) and stationary handle member 16 is formed from two like integral extensions 16A and 16B of housing parts 34A and 34B respectively. The rear ends of housing parts 34A and 34B are formed with rearwardly projecting sections 17A, 17B that combine to form a tang 17 that is shaped so that its rear surface forms a smoothly curved extension of the rear surface of fixed handle member 16, whereby the fixed handle is contoured similarly to that of a 45 cal. Colt automatic pistol. The tang embraces and anchors the web of the hand (i.e., the portion of the hand extending between the thumb and the forefinger) that may be gripping the instrument, permitting the fixed handle to nest comfortably in the user's hand. Housing parts 34A, 34B, including handle portions 16A, 16b, are secured to one another in a conventional way depending on the material of which they are made, e.g., by ultrasonic welding or cementing in the case of plastic and by removable fasteners in the case of metal. For this purpose, and as shown in FIG. 9 which presents a side elevation of the inner side of the right hand housing half 34B, molded energy director strips 35 are provided to facilitate ultrasonic welding (assuming that the handle parts are made of a suitable plastic material such as a polycarbonate). To facilitate assembly, a plurality of registration pins, two of which are shown at 37, are provided in housing part 34B, for insertion into correspondingly located shallow blind registration holes (not shown) in housing part 34A.

Housing 34 has an elongate cylindrical gear tube chamber 42 formed by elongate matching semi-cylindrical recesses 42 in housing parts 34A and 34B (note that FIG. 9 shows only the right hand half 34B of the handle housing). For convenience of illustration and description, the matching recesses or cavities in handle housing halves 34A, 34B, and the chambers or bores formed by such recesses or cavities, are identified by the same numerals, e.g., recesses 42 form chamber 42. Housing parts 34A and 34B also have aligned semi-cylindrical cavities 30 that combine to form an elongate bore in which the rear or proximal end of inner shaft 10 is secured, e.g., by a press fit, cementing or other interlocking means such as a pin as shown at 49. Forwardly of gear tube chamber 42 the housing parts 34A and 34B have aligned semi-cylindrical recesses 44 that combine to form a counterbore that is coaxial with and intersects chamber 42 and has a diameter just large enough to allow shaft 8 to make a close sliding fit therein. Gear rack tube 36 is sized to make a close sliding fit in chamber 42, and has a substantially shorter length than that of chamber 42 so as to allow it to be reciprocated between the two limit positions shown in full and dotted lines in FIG. 9. The two housing parts 34A and 34B have matching recesses 46 (FIG. 9) which form a slot that intersects the gear rack tube chamber 42 at the six o'clock position, so as to provide an axially elongate opening to accommodate handle member 14 between the forward sections of the two fixed handle parts 16A, 16B. Preferably pivot pin 18 is a cylindrical projection that is molded as an integral part of one of the two housing parts 34A, 34B and seats in a cavity located in the opposite housing part. However, pivot pin 18 may take the form of a separate threaded pivot pin that passes through aligned holes in the two housing parts and handle member 14, with a nut or other means (not shown) holding the pivot pin in place.

Movable handle member 14 is provided with a curved set of gear teeth 38 which engage gear rack teeth 40 (FIG. 9) of gear rack tube 36. When movable handle member 14 is rotated about pivot pin 18, the meshing of gear teeth 38 and 40 causes gear rack tube 36 to translate axially in gear rack tube chamber 42. As gear rack sleeve 36 translates within chamber 42, outer tube 8 translates identically since the two parts are affixed to one another. Since jaw piece 2 is rigidly attached to housing 34 via inner shaft 10, jaws 4 and 6 remain at a fixed distance from stationary handle 16. By contrast, outer tubular shaft 8 moves axially toward or away from stationary handle member 16 as gear rack 36 is forced to reciprocate by rotation of movable handle member 14 relative to stationary handle member 16. Thus, outer tube 8 can be extended to override or envelope jaws 4 and 6 to a degree that depends on the relative lengths of outer shaft 8 and inner shaft 10, and the relative rotational positions of movable handle member 14 and stationary handle member 16.

These relative rotational positions are limited in the contractile direction (FIG. 1) by the engagement of the front end of gear rack tube 36 with the forward face of cylindrical chamber 42. In the extensile direction, the relative rotational limit position of handle members 14 and 16 (FIG. 6) is reached when an edge surface 15 of movable handle member 14 abuts the rear edge surfaces 53 of recesses 46 in housing parts 34A and 34B. Other means may be provided or used for determining limits to relative rotation of handle members 14 and 16, e.g., the extensile motion may be limited by engagement of gear rack tube 36 with the rear end face of chamber 42.

Referring now to FIGS. 1, 2 and 6–8, jaw piece 2 has three distinct sections. A rear section 58 has a rectangular cross-sectional configuration that corresponds in shape and size to the rectangular internal configuration of outer shaft 8. Rear section 58 has its rear end face 23 attached rigidly to the front end of inner tube 10. That rear section may be provided with an axial hole 60 to permit ancillary devices to be passed through it to the region of the jaws 4 and 6 via inner tube 10. In such case it is preferred that the rear end of hole 60 be tapered as shown at 24 to facilitate insertion of an ancillary device from inner shaft 10.

If insertion of an ancillary device via hole 60 is to be permitted, the bore 30 and inner shaft 10 must be extended rearwardly so as to intersect the rear end surface of tang 37, so that the open rear end of shaft 10 will be accessible as a port through which the ancillary device may be inserted. This aspect of making the inner shaft accessible at the back side of housing 34 is disclosed in my prior copending application Ser. No. 07/869,535 and is exemplified by the modification shown in FIG. 20.

Forward of rear section 58, jaw piece 2 divides into two (as shown) or more flexible cantilevered spring-like leaves 62, 64 which comprise the center section of jaw piece 2.

Further forward of rear section 58, the leaves 62, 64 thicken into the form of relatively inflexible jaws 4 and 6, the latter forming the front section of jaw piece 2. The form and shape of the jaws may be varied. In this case, jaws 4 and 6 are shown as being serrated for purposes of grasping tissues securely. However, jaws 4 and 6 can assume many other physical forms, e.g., they may be smooth, tapered, grooved, toothed and/or curved. It should be observed that in their unrestrained state (FIG. 8) leaves 62, 64 diverge from rear section 58 at a substantial angle. Because of the angle of divergence between leaves 62 and 64, there is a considerable gap between the tips of jaws 4 and 6 in their free state. This gap is sized to accommodate a blood vessel or a suitable thickness of tissue, or some other item such as a needle or needle holder, that is to be grasped or otherwise manipulated.

Leaves 62, 64 are long enough and thin enough to be elastically flexible over the range of closing motion depicted sequentially in FIGS. 8, 7 and 1. The length and thickness of leaves 62 and 64 are carefully dimensioned since the proper functioning of the jaws is strongly dependent upon proper selection of these parameters. Leaves 62 and 64 are not straight. Instead, in their free or unrestrained state (as shown in FIG. 8), leaves 62, 64 are seen to arc in a convex manner away from each other where they join rear section 58. However, just rearward of the junction of leaves 62 and 64 with jaws 4 and 6, leaves 62, 64 undergo an opposite inflection so as to arc in a concave manner toward each other. Leaves 62, 64 are sufficiently wide to resist strongly any lateral deflection, i.e., deflection normal to the plane of FIG. 8. If leaves 62, 64 are made of a metal such as steel, they are heat treated so that they will not undergo permanent deformation, even if forced open considerably more than shown in FIG. 8. However, leaves 62 and 64 are not so hard or brittle that they are prone to fracture if so deformed. Jaws 4 and 6 can be formed so that one of them may be connected to rear section 58 by a leaf 62 or 64 as described above, while the second leaf may be thicker and hence stiffer or more inflexible all the way to its junction with rear section 58, with the result that the thick-leaved jaw remains relatively motionless even when the thin-leaved jaw deflects as shown in the drawing. If desired, multiple pairs of jaws may be provided, with all of the jaws having flexible spring leaf sections 62, 64, or one or more pairs of jaws may be attached to relatively inflexible leaf sections, and one or more pairs of jaws 6 may be attached to relatively flexible spring leaf sections.

Jaw piece 2 can be fabricated from a piece of square section spring steel or a steel blank of round cross-section, in which case it might be split into three or more jaws, instead of the two opposed jaws shown in the drawings.

As disclosed in my prior copending application Ser. No. 07/869,535, where it is designed to provide an instrument that enables the cutting or dissecting of tissue, one of the jaws may be provided with cutting means in the form of a blade that is received in a slot in the second jaw. Such a blade allows tissue being grasped by the jaws to be cut by the action of the blade. Also as disclosed in my prior copending application Ser. No. 07/869,535, the blade may be designed so as to project forwardly beyond the front ends of the jaws, whereby the instrument may also be used for making an incision.

The instrument of FIGS. 1–9 also is provided with ratchet-type locking means for locking the two jaws against opening movement. This ratchet-type locking means comprises a set of ratchet teeth 71 on sleeve 36 that are in diametrically opposed relation with gear teeth 40. As shown in FIG. 9, teeth 71 have a sawtooth configuration as is required for the ratchet-like action hereinafter described. Teeth 71 are engaged by a pawl 73 which is in the form of a leaf spring. The mating housing halves 34A, 34B have like recesses which form a contoured chamber for pawl 73. The proximal (rear) ends 76A of these recesses are narrowed so as to snugly receive and retain the contoured rear end 73A of the pawl, while their distal (forward) ends 76B are wider (as viewed in FIG. 9) than the thickness of the forward straight end 73B of the pawl, so as to allow the pawl to be flexed out of engagement with teeth 71. Pawl 73 is formed so that its forward end is biased into engagement with teeth 71, except when cammed into a disengaging position as described hereinafter. Teeth 71 are oriented so as to (1) be able to effect a camming force on pawl 73 in a direction to permit gear rack tube 36 to move forwardly, and (2) intercept the pawl so as to obstruct rearward movement of gear rack tube 36.

Figure 10:
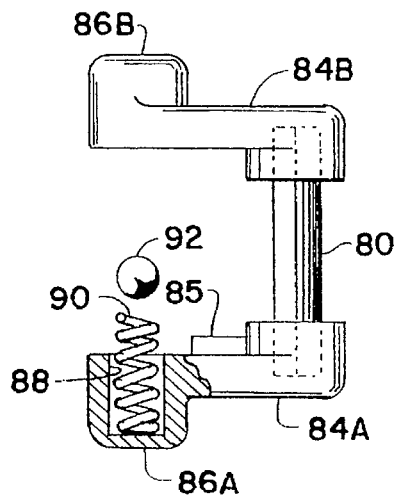
FIG. 10 is a plan view, partially in section, of a portion of the locking mechanism sub-assembly.
Figure 11:
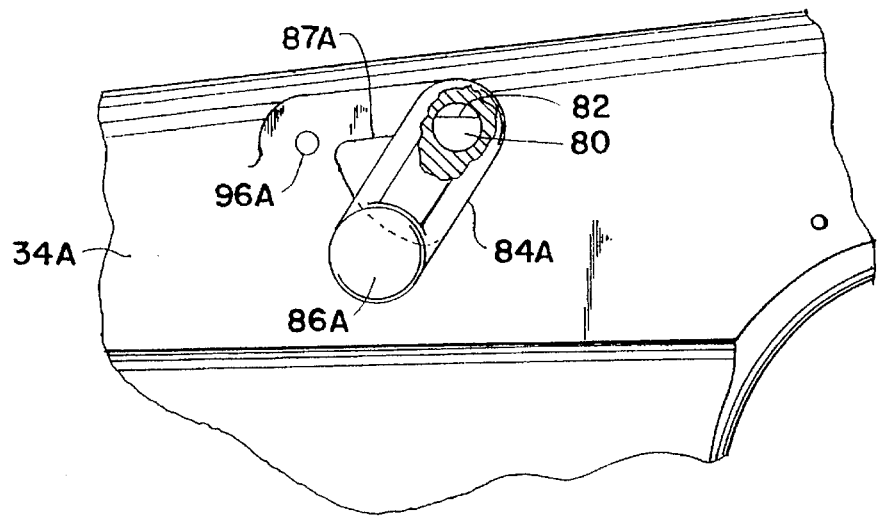
FIGS. 11 and 12 are fragmentary side elevations showing two alternative positions of the locking mechanism.
Figure 12:
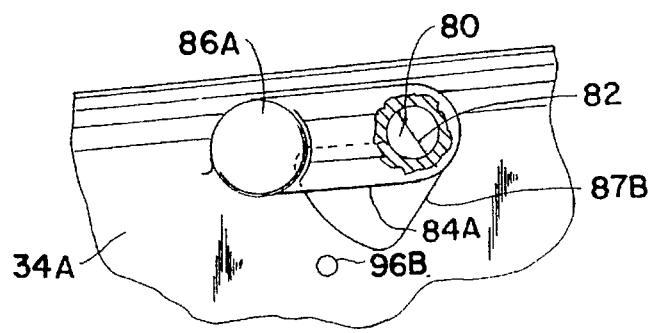

Associated with pawl 73 is a cam-type unlocking means comprising a cam in the form of a pin 80 having a flat surface 82 (FIGS. 9 and 11). Pin 80 extends through and is rotatable in aligned holes formed in the mating housing halves 34A, 34B. Secured to the opposite ends of pin 80 are two levers or arms 84A, 84B having knob-like projections 86A, 86B formed on their free ends. The confronting surface of handle part 34A has a shallow triangularly-shaped recess 87 (FIG. 10) having upper and lower edge surfaces 87A and 87B (FIGS. 11 and 12). Lever 84A has a portion 85 (FIG. 10) that extends into that recess so that the lever's rotational movement about the axis of pin 80 is limited by interception of portion 85 by edge surfaces 87A, 87B.

Lever 84A has a blind hole 88 in its free end to accommodate a small compression spring 90. A small ball 92 is seated in the end of spring 90 and is captivated between the spring and the outer surface of housing half 34A. The latter has two small angularly spaced circular recesses 96A, 96B each sized to accommodate a portion of ball 92. Recesses 96A, 96B coact with ball 90 to lock lever 84A in one or the other of its two limit positions as determined by end edge surfaces 87A, 87B. Obviously, spring 90 and ball 92 may be replaced by making lever 84A flexible and molding a hemispherical protuberance on the end of the lever in position to alternately engage recesses 96A, 96B.

The angular relationship of levers 84A, 84B to the flat surface 82 of cam pin 80 is set so that when the levers are in the position of FIGS. 1 and 11, with ball 92 pressed by spring 90 into recess 96B, the flat surface 82 will be in the horizontal position shown in FIG. 9 and 11, with the result that it will not engage pawl 73 or at least not bias the pawl out of engagement with teeth 71. However, when the unlocking levers are rotated to the position shown in FIGS. 6 and 12, cam pin 80 will engage pawl 73 and cam it out of engagement with teeth 71, thereby allowing spring 45 to push gear sleeve 36 rearwardly to the dotted line position shown in FIG. 9. This places the handle members in the "jaws open" position shown in FIG. 6 and also allows the two handle members to be moved freely back and forth between that "jaws open" position and the "jaws-closed" position of FIG. 1.

Whenever the surgeon wants to be able to lock the jaws in grasping relation with tissue or another object, all that he need do is move levers 84A, 84B to the ratchet enabling position of FIGS. 9 and 11, whereupon as handle member 14 is squeezed toward handle member 16 (see FIG. 9), pawl 73 will ride from one tooth to another of teeth 71 as gear sleeve 36 is advanced toward the forward jaws-closed position (FIG. 1). When the surgeon stops squeezing the two handle members, the bias on outer tube 8 exerted by the resilience of jaws 4 and 6, and/or the force of spring 45, will urge gear sleeve 36 rearwardly again, but pawl 73 will interfere with that action by virtue of its engagement with one of the ratchet teeth 71.

As disclosed in my prior copending application Ser. No. 07/869,535, the instrument shown in FIGS. 1–3 may be adapted for monopolar electrosurgery, simply by connecting an appropriate source of electrical power to inner shaft 10. My prior copending application Ser. No. 07/869,535, also discloses the concept of modifying the instrument shown in FIGS. 1–3 for bipolar electrosurgery.

Referring now to FIGS. 2, 5 and 9, the illustrated preferred embodiment is adapted for electrosurgery purposes. For this the two mating halves 34A, 34B of the handle assembly are provided with a pair of matching semi-cylindrical recesses 100 that form a cylindrical passageway 100 at the proximal (rear) end of the instrument. Passageway 100 intersects a contoured chamber 102 formed by matching recesses 102 in the two halves 34A, 34B of the handle assembly. The recesses 102 are shallower than the recesses 100. Chamber 102 is generally L-shaped, having an angular extension 102A at its proximal end.

Disposed in chamber 102 is an electrically-conductive generally P-shaped spring-like contact member 106 having a forward end 106A that is configured to retain it in the forward angular extension 102A of chamber 102. The remainder or rear section 106B of the contact is formed with a convex curvature so that it normally protrudes into passageway 100. The forward curved section 106A and the proximal or rear end section 106B of contact 106 both make direct contact with inner shaft 10. Contact member 106 is captivated in the forward end 102A of chamber 102 so that it cannot move, while the axial length of chamber 102, i.e., the dimension extending parallel to the axis of inner shaft 10, exceeds the corresponding length of contact member 106 whereby to allow the contact member to expand longitudinally as it undergoes bending under the influence of an electrically conductive connector member 110 that is inserted in passageway 100.

Connector member 110 may take various forms. Preferably it is a conventional form of connector element commonly used to electrify surgical instruments. For example, it is preferred that connector member 110 be bifurcated at both ends, having a like pair of divergent spring-like contact fingers 112, 114 at its opposite ends. The fingers are shaped and sized so that they must be compressed toward one another in order to be received in mating passageway 100, e.g., fingers 112 are compressed radially in order to made a tight fit in passageway 100. The center portion of connector member 110 is oversized so as to form a cylindrical peripheral flange 120. The latter is sized and shaped to engage a shoulder 122 formed by a counterbore 124 in the two mating halves 34A, 34B in the handle assembly. Engagement of flange 120 with shoulder 122 limits the extent to which the diverging fingers 112 can be inserted into the handle assembly. Fingers 122 are long enough to engage the convex rear portion 106B of contact member 106, causing that convex portion to become flattened and to expand lengthwise in chamber 102. The direct contact between connector member 110 and contact member 106 is substantially constant due to the spring-like action of the contact member which causes it to bear tightly against the connector member. The spring-like fingers 114 on the outer end of connector member 110 are intended to be inserted into a female connector (not shown) which is connected by a suitable insulated connecting cable (not shown) to a suitable electrical generator (not shown), whereby an electrical potential is transmitted via contact member 106 and inner shaft 10 to jaw piece 2, thereby enabling the tool to be used for monopolar electrosurgery. Obviously, connector member 110 may be removed from the instrument when no electrosurgery capability is required.

It is preferred that handle member 14, and also housing 34 with fixed handle member 16, be molded of a plastic material, e.g., a polycarbonate or ABS, although they could be formed of other materials.

Outer shaft 8 and inner shaft 10 may be made of various materials, including a metal such as stainless steel or a synthetic plastic such as TEFLON. Preferably outer shaft 8 is made of a plastic material which is inert to the human body, while inner shaft 10 is preferably made of a non-corrosive electrically conductive metal, e.g., a stainless steel.

Referring now to FIGS. 13 and 14, in the case where the instrument is adapted for monopolar electrosurgery, e.g., electro-cauterization, and outer shaft 8 is made of a synthetic plastic material such as TEFLON, it is preferred to reduce the outer diameter of the front (distal) end of shaft 8 to accommodate a metal reinforcing sleeve or ferrule 130. This use of a reinforcing ferrule is disclosed in my prior copending application Ser. No. 07/869,535 and also is shown at 66 in FIGS. 7 and 8. Unfortunately, the presence of metal sleeve 130 creates the possibility of capacitive coupling between the electrified inner shaft 10 and sleeve 130, with the possible undesirable result that electrical energy may be passed to the patient as a result of such capacitive coupling.

To avoid such a result, an electrical insulation may be applied over reinforcing ferrule 130. The electrical insulation may take the form of a coating of an electrically non-conducting material of sufficient thickness and insulating capability to prevent transmission of electrical energy to the patient via ferrule 130, e.g., a solvent-deposited thin film of a non-conductive polymer, e.g., TEFLON. Alternatively, as shown in FIGS. 13 and 14, the electrical insulation may take the form of a shrink tubing 134 of polyethylene, TEFLON or some other suitable synthetic plastic having a heat shrink capability. If desired, the insulation may extend for the full length of the portion of outer shaft 8 that extends forwardly of the handle assembly, or it may extend only for the full length of reinforcing sleeve 130, or any in-between length that assures full covering of the reinforcing sleeve. Preferably as shown in FIG. 13, the front end edge of reinforcing sleeve 130 is set back from the front end edge of shaft 8 so as to expose a limited area 140 of the front end of shaft 8, whereby as the plastic shrink tube contracts, it engages and adheres to that exposed area and thereby provides a shrink wrap retaining ring 142 that better secures reinforcing sleeve 130 to outer shaft 8.

It should be noted that the forward end section of shaft 8 may have a rectangular inner configuration as shown at 146 and the forward end of inner shaft 10 may have a matching outer surface configuration.

FIGS. 15–19 disclose a further embodiment of the invention that is adapted for bipolar cauterization purposes. Although this embodiment is shown as including a ratchet-type locking mechanism as disclosed in FIG. 9, it is to be appreciated that the ratchet-type locking mechanism may be omitted without altering the capability of the instrument to satisfy bipolar cauterization purposes.

Referring now to FIGS. 15–19, the bipolar version of the invention is designed to satisfy the need for bipolar electrosurgery which is gaining favor because, unlike monopolar electrosurgery, the surgical candidate's tissue is not used as ground. For example, in bipolar electrosurgery involving the use of a grasper, the two jaws of the grasper are electrically charged so that there is an electrical potential between them, usually by high frequency AC electricity provided by special generating means available commercially for surgical applications. Bipolar electrosurgery has the advantage of reducing the possibility of inadvertent burning of the patient or surgeon.

In the embodiment shown in FIGS. 15–19, the handle assembly is generally similar to the handle assembly shown in FIGS. 1–9, except for the differences hereinafter noted. A first difference is that the handle assembly includes a pair of terminal pins 150 and 152 that are anchored in suitable recesses formed in the two mating halves 34A, 34B of the handle assembly. These terminal pins are designed to receive a bipolar female connector 154 having a pair of cables 156 and 158 that are coupled by the female connector to terminal pins 150 and 152 respectively. As hereinafter noted, terminal pin 150 is the electrically "hot" terminal, while terminal pin 152 is the electrical "ground" terminal. Terminal pin 150 is connected by insulated wire cable 162 to the jaw assembly in the manner hereinafter described. Cable 162 extends through a passageway defined by a pair of like inclined recesses 166 that leads from terminal pin 150 to a hollow inner shaft 210.

Figure 15:
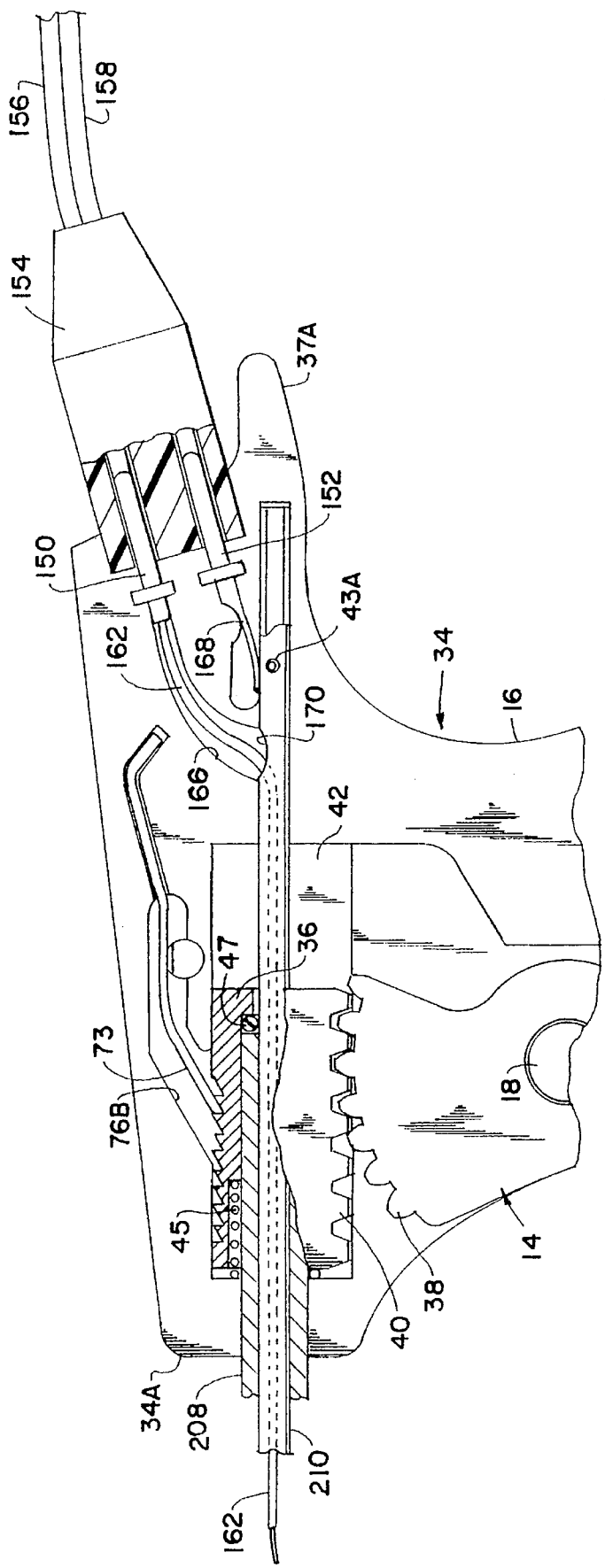
FIG. 15 illustrates another form of the invention and constitutes a fragmentary sectional view in side elevation of the handle portion of an instrument having bipolar cauterization capability.

Referring still to FIG. 15, inner shaft 210 is made of metal and corresponds to the inner shaft 10 of FIGS. 1–9. Shaft 210 is anchored in the handle assembly by suitable means, e.g., by a roll pin 43A (FIG. 15). Inner tube 210 is provided with a side port 170 through which the insulated wire 162 can pass into its interior. The second "ground" terminal pin 152 is provided with a leaf spring extension 168 on its inner end, with the leaf spring extension being biased into direct physical and electrical contact with the outer surface of the proximal end of inner shaft 210, as shown in FIG. 15.

The outer tube or shaft 208, which is identical to outer tube 8 of the embodiment of FIGS. 1–9, extends into the handle housing 34 and is anchored to the tube sleeve 36 in the same way as tube 8 in the embodiment of FIGS. 1–9.

Referring now to FIGS. 16–19, outer tube 208 is reinforced by a ferrule 230 which corresponds to ferrule 66 of FIGS. 7 and 8 and ferrule 130 of FIG. 13. Hollow inner shaft 210 is provided with an enlarged rectangular end section 232 which is sized and shaped to make a snug sliding fit in the rectangular bore 233 of the front end of outer tube 208, in the same fashion as the bore in outer shaft 8 of FIGS. 1–9 receives the rectangular cross-section rear end of jaw piece 2.

As seen best in FIG. 19, the forward end of the rectangular end section 232 of metal shaft 210 is open, and one of its four sides is provided with an elongate axially extending slot 234. Mounted within end section 232 of inner shaft 210 is an insulator block 240 which preferably is made of a molded plastic. As seen best in FIGS. 16 and 19, insulator block 240 is provided with an elongate body section 242 of rectangular cross-sectional configuration and a relatively thin tongue-like front extension 244. Additionally, the insulator block has a pair of bosses 246 projecting from each of its two opposite side surfaces. The insulator block also has a cavity 250 and a groove 252 which communicates with and intersects that cavity. The rear end of insulator block 240 is reduced in cross-sectional size so as to form a pair of L-shaped shoulders 258. Additionally, insulator block 240 has a pair of spacer bosses 260 intermediate cavity 250 and shoulders 258. It also has a pair of grooves or slots 266A, 266B on opposite sides of its reduced cross-sectional size rear end section for the purpose of receiving portions of the hollow front end 232 of inner tube 210 for anchoring purposes as hereinafter described.

Still referring to FIGS. 15–19, the jaw piece or head comprises a pair of leaf-spring elements 62A and 64A which correspond in function to the members 62 and 64 of the embodiment of FIGS. 1–9, except as hereinafter described. The forward ends of these leaf-spring elements carry jaw members 4A and 6A. While the jaw members may be formed as integral portions of the leaf-spring elements, like the jaws 4 and 6 described in connection with FIGS. 1–9, it may be preferred to have jaws that are preformed as separate elements and which are secured to the leaf-spring elements by conventional means, e.g., by peening, welding or cementing. Thus, as shown in FIGS. 16–18, the jaws may comprise separately fabricated jaw members 4A and 6A, with each jaw member comprising a plurality of round bosses 272 which protrude into and make a press fit, or else are peened over, in mating holes 274 provided in each of the leaf-spring elements. Each of the two leaf-spring elements is formed with a pair of elongate holes 280 that are sized to snugly accommodate the bosses 246.

Still referring to FIGS. 16–19, the insulated cable 162 extends along the interior of inner shaft 210 and at its forward end it is soldered or otherwise attached to the hot leaf-spring element 64A. The connection of the cable to the leaf-spring element is illustrated by the solder joint 276.

The leaf-spring elements are mounted to the insulator block, with bosses 246 fitting into elongate apertures 280 in the leaf spring elements, and the insulated cable 162 extending along groove 252, with the protruding solder joint 276 being accommodated by the cavity 250 in the insulator block. The rear end of insulator block 240 and the tang 63 on leaf-spring element 62A, are inserted into the open end of the hollow extension 232 of inner shaft 210, and the rear end of block 240 is secured in place by mechanically deforming opposite sides of hollow extension 232 so as to form dimples 284 (FIG. 18) that are received in the slots 266A, B of the insulator block. Engagement of the dimples with the sides of the slots prevents separation of the insulator block 240 and the two leaves from shaft 210. The tang 63 is constructed so that in its as-formed (unrestrained) state its free end projects laterally of its fixed end (i.e., the point where it joins leaf 62A), so that when the tang is inserted in slot 234, it will be deformed laterally by engagement with a longitudinal side surface of the slot so as to make good electrical contact with shaft 210.

As a result of the foregoing construction, when the external cables 156 and 158 are coupled to a source of electrical potential so that the cable 162 becomes a hot wire and terminal pin 152 becomes a ground connector, the leaf-spring elements 62A, 64A and the jaws 4A, 6A become electrified, with jaw 4A being at ground potential and jaw 6A being at a different potential, whereby when the jaws are brought into contact with tissue, bipolar cauterization can be performed.

The advantage of having the insulator block 242 formed with a thin protruding tongue 244 is that the tongue prevents the leaves 62A, 64A from touching one another physically or electrically, and thereby avoids direct electrical contact (i.e., short circuiting) between the jaws.

If it is desired to use the bipolar instrument of FIGS. 15–19 in the monopolar mode, the "hot and "ground" terminals 150 and 152 may be joined, as by an external bus or switch (not shown), or controls (also not shown) within the electrosurgical generator. Consequently, the instrument of FIGS. 15–19 is adapted for either monopolar or bipolar electrosurgery or else, by detaching connector 154, it may be used without any electrosurgical capability.

Figure 20:
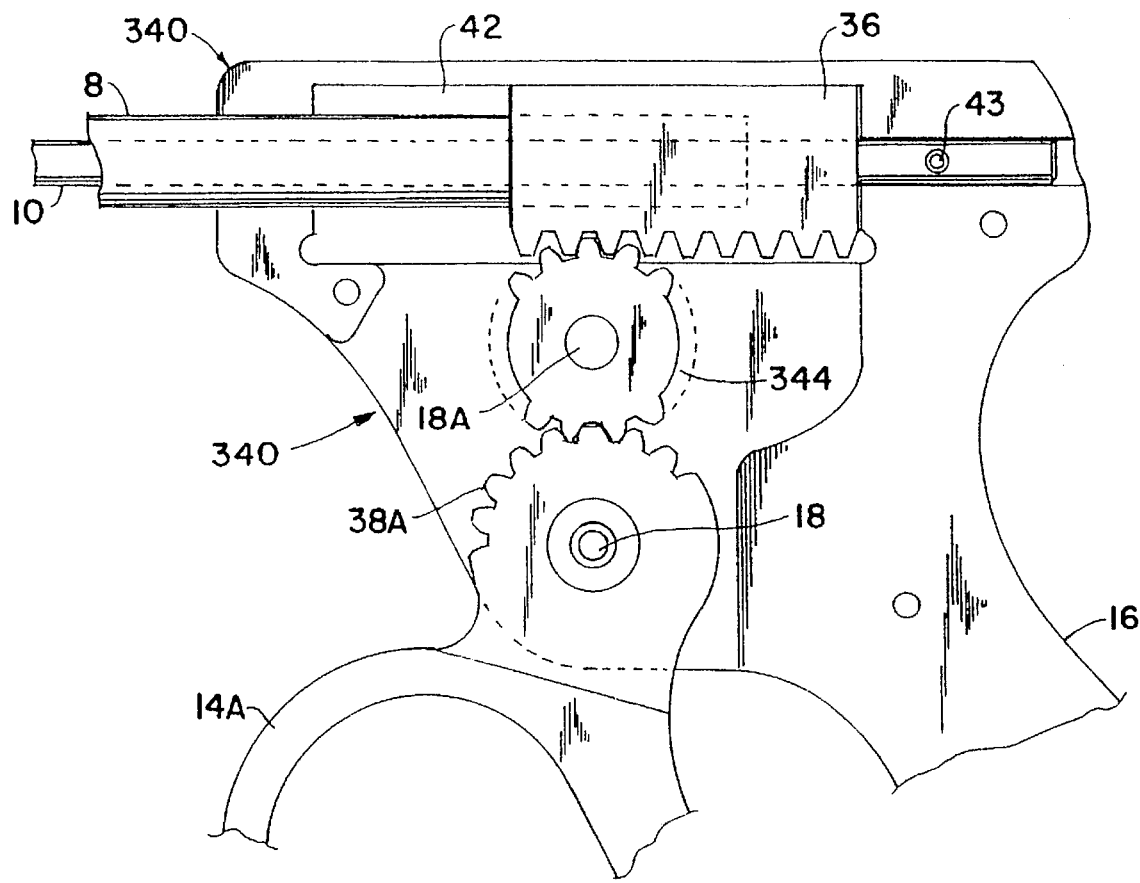
FIG. 20 is a fragmentary side elevation, partially in section, illustrating another embodiment of the invention involving a reversing gear.

FIG. 20 is a modification of the invention whereby forward telescoping movement of outer shaft 8 relative to inner shaft 10 is achieved when the handles are moved away, rather than towards one another. For convenience of illustration, the ratchet mechanism and the return spring 45 shown in FIG. 9 have been omitted from FIG. 20. However, it is to be understood that the embodiment of FIG. 20 may include a ratchet mechanism and return spring as disclosed in FIG. 9. Also, although not shown, the embodiment of FIG. 20 may be electrified for cauterization purposes in the manner of the embodiments of FIGS. 1–9 and 15–19.

Referring more particularly to FIG. 20, handle housing 340 is generally similar to the handle housing 34 shown in FIG. 9, except that a second pivot pin 18A is molded as an integral part of one of the two handle halves, and an idler gear 344 is rotatably mounted on the second pivot pin. Additionally, the upper end of movable handle member 14A differs from handle member 14 shown in FIG. 9 in that it is shorter and has a plurality of teeth 38A arranged in a circularly curved array having a smaller pitch radius. The gear teeth 38A on handle member 14A mesh with the teeth of gear 344, and the teeth of gear 344 in turn also mesh with the teeth of gear rack tube 36. Consequently, when the handle 14A is pivoted forwardly (clockwise) on the axis of pivot pin 18, as viewed in FIG. 20, the gear rack tube 36 will move forwardly in chamber 42 to effect closing of jaw piece 2.

Figure 21:
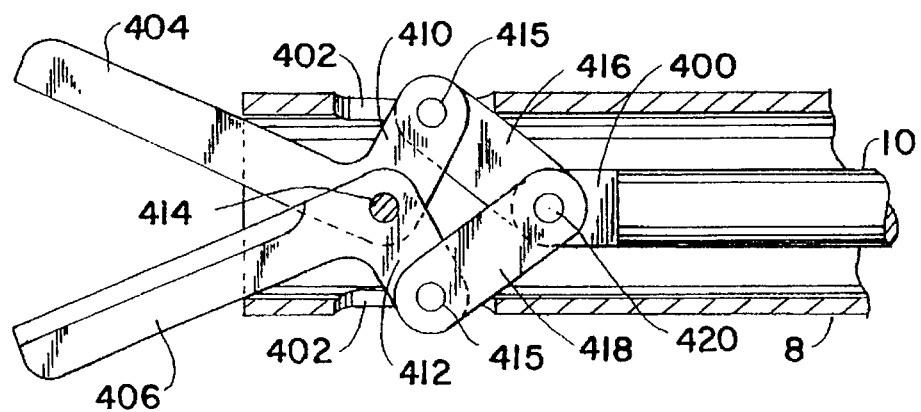
FIG. 21 is a longitudinal sectional view in elevation of a form of scissors-type head that may be combined with a handle mechanism provided by the present invention.
Figure 22:
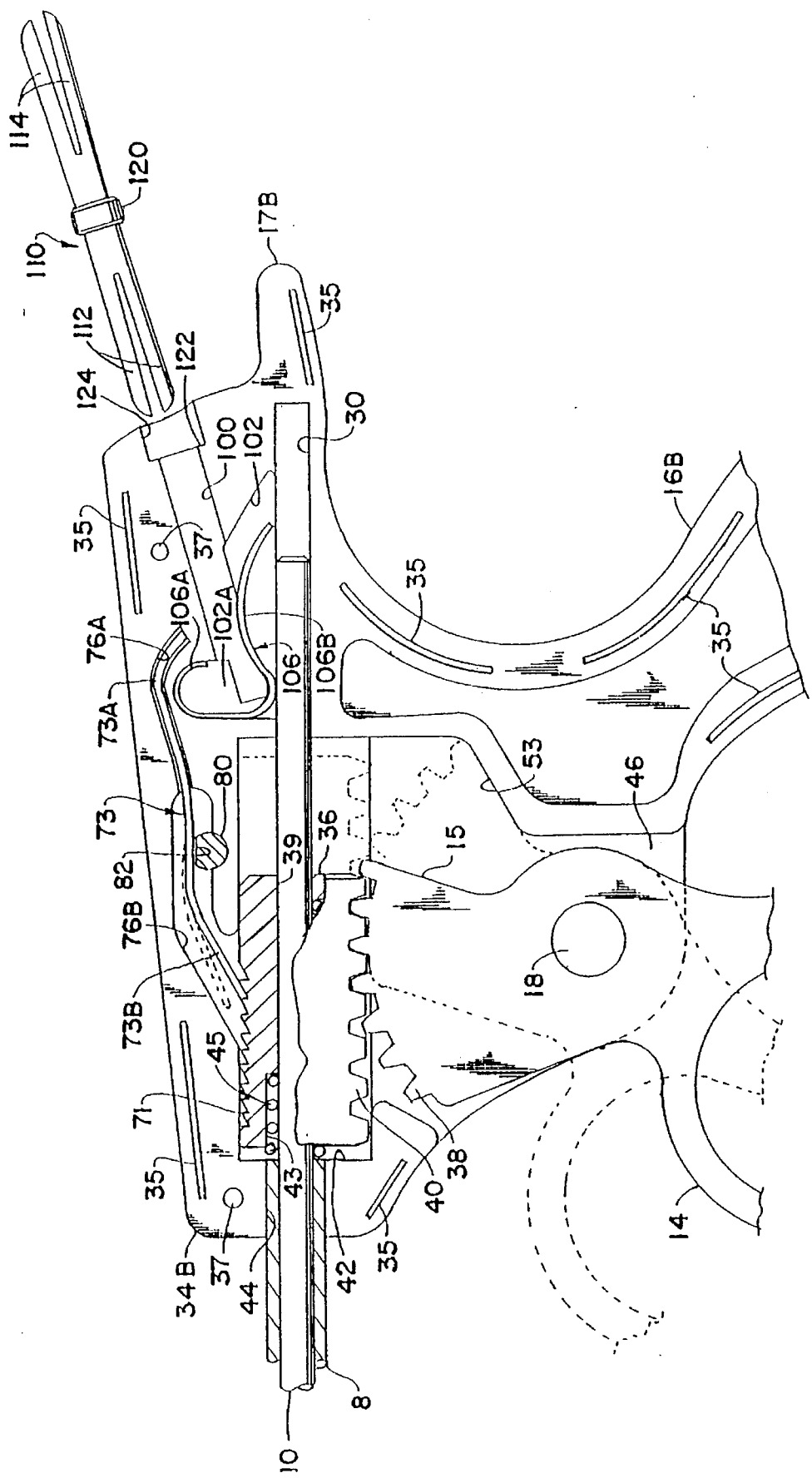
FIG. 22 illustrates a further embodiment of the invention adapted for use with the head of FIG. 21.

FIG. 21 illustrates a scissors head that may be used, for example, with the embodiment of FIG. 22. In this case the inner member 10 is in the form of a solid rod having a tongue-like extension 400 at its forward end, and the outer tube 8 is provided with a pair of diametrically opposed clearance holes 402 that are elongated parallel to the tube's axis. Attached to rod 10 is a scissors head comprising a pair of scissors blades 404 and 406 having angular extensions 410 and 412 respectively at their rear ends. Blades 404 and 406 are pivotally attached to outer tube 8 by a pivot pin 414 whose opposite ends are in the tube. The outer ends of angular extensions 410 and 412 are pivotally coupled by pivot pins 415 to the forward ends of two links 416 and 418 respectively. The rear ends of links 416 and 418 are pivotally attached to tongue extension 400 by a pivot pin 420. In essence extensions 410 and 412 and links 416 and 418 form a toggle assembly.

Referring now to FIG. 22, tube 8 and rod 10 are attached to a handle assembly which is like the one shown in FIG. 9, except that in this case the rod 10 is free to slide in bore 30, and the rear end of hollow tube 8 is anchored to the handle assembly. Moreover, the rear end of tube 8 does not extend into chamber 42 and instead gear rack tube 36 is affixed to rod 10 so that it and rod 10 move together when the handle mechanism is operated.

An instrument combining the structures of FIG. 21 and 22 provides a scissors whereby when the handle 14 is moved from its open or forward (dotted line) position to its closed or rearward (solid line) position, gear teeth 38 will act on gear teeth 40 to drive gear rack tube 36 and hence rod 10 forward relative to tube 8, with the result that blades 404 and 406 will close on one another to provide a cutting action on any intervening tissue. Opposite movement of handle 14 will cause the blades to return to open position. Holes 402 are sized so as not to interfere with movement of extensions 410, 412 and links 416, 418.

Obviously the scissors blades shown in FIG. 21 may be replaced by jaws or other members when it is desired to provide a grasper or other instrument.

Figure 23:
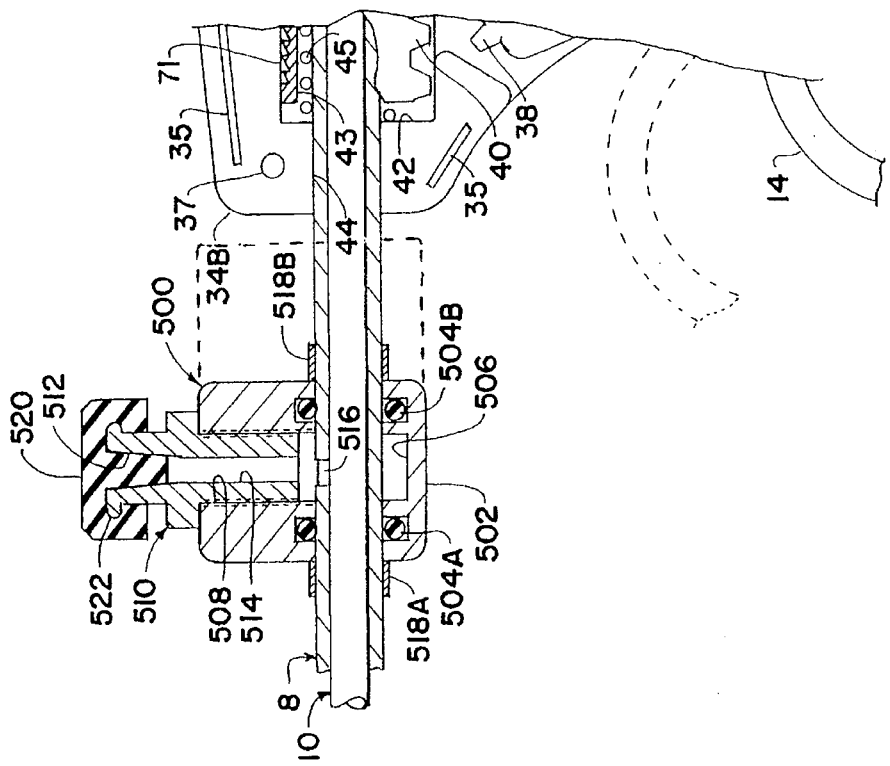
FIG. 23 is a view of a modification of the invention designed to provide an irrigation and cleaning function.
Figure 24:
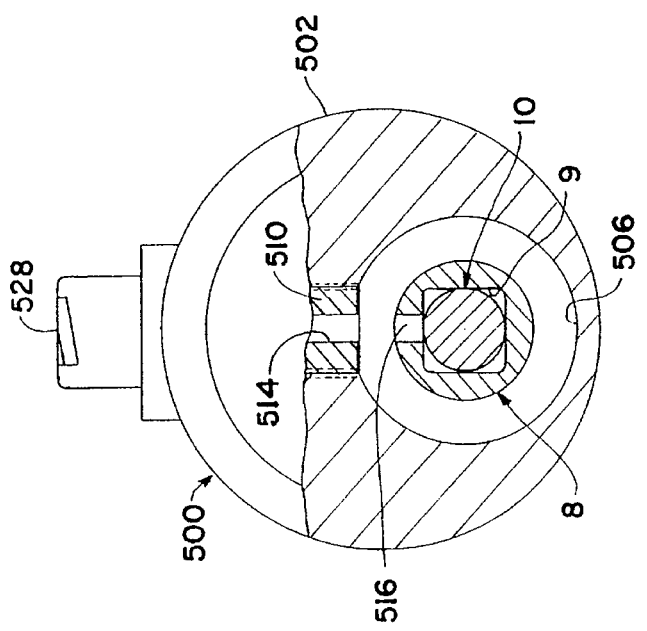
FIG. 24 is an enlarged cross-sectional view taken through the center of the irrigation adapter of FIG. 23.

FIGS. 23 and 24 relate to a modification of the apparatus of FIGS. 1–10 and illustrate how instruments made according to the invention may be provided with an irrigation and/or cleaning function. In the embodiment of FIGS. 1–10, the inner shaft has a round cross-section while the outer shaft 8 has a substantially square axial bore 9 within which shaft 8 reciprocates. Referring to FIG. 24, when shaft 10 is disposed in outer shaft 8, four generally triangular passages are formed between the four corners of bore 9 and inner shaft 8. As a result, when the instrument is used in a surgical procedure, body fluids and bits of solid matter may tend to fill those passages. This filling action may be due to "wicking" (capillary action) or to the positive pressure automatically maintained in a body cavity during endoscopic surgery such as laparoscopy. The fluids that enter the spaces between the inner and outer shafts may include irrigating fluids such as a saline solution. It is to be appreciated also that such inflow of body or other fluids or bits of solid matter will occur with any combination of inner and outer shafts where sensible space exists between the outer surface of the inner shaft and the inner surface of the outer shaft, as, for example, where the shafts have similar cross-sectional configurations but have a small clearance between them. The likely inflow of fluids or bits of tissue or other matter presents a problem due to the possibility that after surgery they may dry and/or harden so as to leave residues that inhibit free operation of the instrument and/or present sterilization problems. Therefore, they should be removed if the instrument is to be reused.

FIGS. 23 and 24 show a modification which not only facilitates cleaning but also permits irrigation. The modification consists of providing a collar assembly 500 that comprises a collar 502 having a first through hole sized to allow it to be slipped over outer shaft 8, a pair of grooves at opposite ends of the through hole in which are disposed O-rings 504A, 504B, an annular cavity 506 surrounding shaft 8, and a second hole 508 that intersects cavity 506 and is threaded to receive a fitting 510 for introducing fluid to or receiving fluid from cavity 506. By way of example but not limitation, fitting 510 may be a conventional Luer fitting as shown that is characterized by an outward taper 512 at the outer end of its internal passageway 514. Collar 502 is mounted so that it cannot move axially relative to outer shaft 8 and also so that its annular cavity 506 communicates with one or more radial holes 516 in outer shaft 8, the hole(s) 516 being located so as to communicate with the space(s) between shafts 8 and 10. The collar is positioned on shaft 8 so that it will not prevent (by engagement with housing posts 34A, 34B) the shaft from reaching its intended rear limit position when moved rearwardly by operation of the handle mechanism as previously described. In FIG. 23, the rearmost position of collar 512 is shown in dotted lines.

The collar may be locked against relative axial movement by various means, e.g., by sections of heat shrink tubing as shown at 518A, B which make a tight connection to shaft 8, or by retaining rings or other suitable components (not shown) that will be obvious to persons skilled in the art. However, the collar is not fixed against rotation relative to shaft 8, but instead its orientation about the axis of shaft 8 is selectable by the surgeon. Whatever orientation is selected by the surgeon is maintained by the friction between O-rings 504A, B and shaft 8. The O-rings are sized so that the torque required to rotate the collar on shaft 8 is just enough to permit the surgeon to rotate it without great effort, while assuring that the collar will remain firmly in any selected position after it is released by the surgeon. The O-rings 504A, B also function to prevent fluid from leaking out of the collar assembly. A snap-type cap 520 cooperates with a peripheral flange 522 on fitting 510 to prevent fluid leakage from the fitting.

For cleaning purposes when the tool is not being used in surgery, cap 520 is removed and a syringe or another source of pressurized cleaning fluid is attached to fitting 510. Preferably, a syringe (not shown) is used which has a tapered male section that fits into the tapered outer end 512 of fitting 510. Preferably the syringe has a threaded means which lockingly engage two or more threaded ears 528 formed on collar 502, whereby to lock the syringe and collar together with the tapered male portion of the syringe making a tight connection with the female tapered portion 512 of the fitting.

Having connected the syringe to the apparatus, and having previously loaded the syringe with appropriate cleaning fluid, the syringe is forcefully discharged, with the result that cleaning fluid is forced into hole 514, then to annular cavity 506, and then into hole 516 of outer shaft 8. If pressure is maintained, cleaning fluid will forcefully eject body fluids and solid matter remaining between shafts 8 and 10. The materials will be ejected distally only, i.e., will be forced out of the tip end of the instrument. Turbulence proximally of collar assembly 500 will dislodge and carry away materials located in this region.

The progress of surgery is often aided if a saline solution or another irrigating fluid can be introduced at the surgical site. Accordingly, the fitting 510 may be adapted for connection of a flexible tubing connected to a supply of irrigating fluid, with the fluid flowing under pressure through radial ports 516 and the space(s) between shafts 8 and to the surgical site. Alternatively, collar 502 and fitting 510 may be used as a means for withdrawing fluid from the surgical site, using a syringe or another vacuum-applying device to remove such fluid from the surgical site.

To the extent that they are relevant, the constructional features and other teachings provided by my prior U.S. application Ser. No. 07/869,535 are incorporated herein by reference thereto.

The invention provides a number of advantages relevant to construction and use. In addition the invention is susceptible of a number of modifications in addition to the ones herein described. Thus, for example, depending on the construction of the jaw piece, or its replacement by some other head assembly, it is contemplated that the embodiment of FIG. 20 could be modified so that, like the embodiment of FIG. 22, its outer shaft 8 would be fixed to the handle housing and inner shaft 8 could be attached to gear tube 36, so that manipulation of the two handle members would cause the inner shaft to move telescopingly relative to the outer shaft. Of course, the relative limit positions of the two handle members, or associated components, may be determined by means other than those herein described or illustrated. Similarly, the electrical connections may be provided by means other than those herein described or illustrated. Thus, for example, the bipolar instrument of FIGS. 15–19 could be modified by connecting the jaw 4A to an electrically insulated cable (not shown) like cable 162 that runs within inner tube 110 back to and through a side port (not shown) like side port 170 and is connected to terminal pin 152. Also collar 502 and fitting 510 could be combined into a single piece. Still another possible modification is to provide fitting 510 with a check valve (not shown) so that gas pressure or fluids under pressure cannot leak back out of the collar assembly during the cleaning operation or at other times, e.g., when irrigating via fitting 510. If a check valve is provided, cap 520 may be omitted. Both the cap and check valve also serve to prevent foreign matter from entering the instrument via collar 502, from which it might find its way to the surgical site.

Still other modifications will be obvious to persons skilled in the art from the foregoing description.

What is claimed is:

1. A surgical instrument for performing electrosurgery comprising:

a handle housing with a first handle member affixed thereto, and at least first and second concentrically arranged shafts extending longitudinally away from said housing, said second shaft having proximal and distal ends and being affixed to said housing at its proximal end so as to be immobile with respect to said housing, and said first shaft surrounding said second shaft and being arranged to translate longitudinally with respect to said second shaft;

a jaw unit carried by said distal end of said second shaft, said jaw unit comprising at least two jaws, a rear section, and intermediate leaf spring elements connecting each of said jaws to said rear section, said leaf spring elements biasing said jaws so that when said leaf spring elements are unrestrained, said jaws are deployed in angular spaced relation with one another;

said first shaft having a length such that when said first shaft is caused to translate towards the distal end of said second shaft, the distal end of said first shaft will slide over said jaw unit and mechanically cause said jaws to close towards one another;

translation means for causing said first shaft to translate longitudinally relative to said second shaft, said translation means comprising a second handle member mounted for pivotal movement relative to said first handle member, and means coupling said second handle member and said first shaft for causing reciprocal movement of said first shaft relative to said second shaft as said second handle member is pivoted relative to said first handle member, whereby to cause said first shaft to move into and out of jaw-closing relation with said jaws; and electrically-conductive means carried in part by said handle housing for applying an electrical potential to said jaws, whereby an electrical current will flow in tissue engaged by said jaws.

2. An instrument according to claim 1 wherein said electrically-conductive means comprise electrical connector means mounted in said handle housing, and means for electrically connecting said electrical connector means to said second shaft.

3. A surgical instrument according to claim 2 comprising retaining means for releasably retaining said electrical connector means in said housing.

4. A surgical instrument for performing bipolar electrosurgery on tissue comprising:

a housing provided with an internal bore, first and second concentrically arranged tubular elements within said bore, said first and second tubular elements each having a proximal end and a distal end, with said first tubular element being immobile with respect to said housing and said second tubular element being capable of translating axially relative to said first tubular element;

means attached to said housing for causing said second tubular element to translate axially relative to said first tubular element;

a jaw head comprising first and second separately formed jaws, with said jaws being spring biased so as to normally occupy an open position relative to one another;

means connecting said jaw head to the distal end of one of said tubular elements;

said first and second tubular elements being disposed so that they can undergo relative axial movement bidirectionally and so that when said they undergo relative axial movement in a first direction, said second tubular element will force said jaws to close towards one another; and electrically-conductive means carried by said housing for applying an electrical potential to said jaws, said electrically-conductive means being arranged for connection to an external source of electrical power.

5. An instrument according to claim 4 comprising insulation means disposed so as to prevent one jaw from physically contacting the other jaw.

6. A surgical instrument for performing electrosurgery comprising:

a hollow outer shaft having a longitudinal axis, a first proximal end and a first distal end;

a hollow inner shaft coaxially disposed in said outer shaft for reciprocal movement with respect to said outer shaft, said inner shaft having a second proximal end and a second distal end;

means for surgical interaction with animal tissue associated with said first and second distal ends, said surgical interaction means comprising first and second tissue-interacting members movable relative to one another between a first open position and a second closed position by axially directed changes in the relative positions of said first and said second distal ends;

a handle mechanism coupled to said outer and inner shafts for effecting relative axial movement of said shafts and thereby changing the relative positions of said first and said second distal ends lengthwise of said longitudinal axis;

said handle mechanism comprising a first handle member affixed to the proximal end of one of said shafts, driver-responsive means attached to the other of said shafts, a second handle member movable relative to said first handle member between first and second operating positions, driver means carried by said second handle member engageable with said driver-responsive means for effecting reciprocal axial movement of said other shaft relative to said one shaft in response to movement of said first handle member between said first and second operating positions;

unidirectional locking means for locking said first and second handle members against relative movement in one predetermined direction; and electrically-conductive means carried in part by a handle housing for applying an electrical potential across said tissue-interacting members, whereby an electrical current will flow through tissue engaged by said tissue-interacting members.

7. An instrument according to claim 6 wherein said first and second tissue-interacting members comprise first and second electrically conductive jaw members mounted to the distal end of said inner shaft and electrically insulated from one another, and said electrically-conductive means comprises first electrical conductor means connected to said first jaw member and second electrical conductor means connected to said second jaw member.

8. An instrument according to claim 7 wherein said first and second jaw members comprise first and second electrically-conducting leaf spring members and first and second electrically-conducting jaws carried by said first and second leaf spring member respectively, and further including an insulating member attached to the distal end of said inner shaft for supporting said jaw members on the distal end of said inner shaft.

9. An instrument according to claim 7 wherein said inner shaft is electrically conductive and said second jaw member is electrically coupled to said inner shaft.

10. An instrument according to claim 7 wherein said first electrical conductor is a cable that extends along the interior of said inner shaft and is connected to said first jaw member.

11. An instrument according to claim 6 wherein at least one space exists between said outer and inner shafts, and further including means for introducing fluid to or removing fluid from said at least one space.

12. An instrument according to claim 11 further characterized by at least one radially-extending opening in said outer shaft, and a collar assembly surrounding said outer shaft, said collar assembly having a chamber that communicates with said at least one radially-extending opening and a port that permits fluid to be introduced to or removed from said chamber.

13. An instrument according to claim 12 wherein said collar assembly is provided with a fitting that is coupled to said port and is adapted to be connected to an auxiliary device.

14. A surgical instrument comprising:

a hollow outer shaft having a longitudinal axis, a first proximal end, and a first distal end;

an inner shaft coaxially disposed in said outer shaft, said inner shaft having a second proximal end and a second distal end;

means for surgical interaction with animal tissue attached to the distal end of said inner shaft, said surgical interaction means comprising first and second tissue-interacting members movable relative to one another between a first open position and a second closed position by axially directed changes in the relative positions of said first and said second distal ends of said shafts; and a handle mechanism coupled to said outer and inner shafts for effecting relative axial movement of said shafts and thereby changing the relative positions of said first and said second distal ends lengthwise of said longitudinal axis;

said handle mechanism comprising a housing that surrounds the proximal ends of said shafts, means securing one of said shafts to said housing so as to prevent movement thereof relative to said housing, a first handle member affixed to said housing, driver-responsive means attached the other of said shafts, a second handle member, pivot means connecting said second handle member to said first handle member, said second handle member being movable on its pivot relative to said first handle member between first and second operating positions, driver means carried by said second handle member engageable with said driver-responsive means for effecting axial movement of said other shaft relative to said one shaft in response to movement of said second handle member from one to the other of said first and second operating positions; and unidirectional locking means for locking said first and second shafts against relative axial movement in one predetermined direction; and bi-polar electrically-conductive means for applying an electrical potential difference across said tissue-interacting members, whereby an electrical current will flow through tissue engaged by said tissue-interacting members.

15. A surgical instrument comprising:

a handle housing with a first handle member affixed thereto, and at least first and second concentrically arranged shafts extending longitudinally away from said housing, said first and second shafts each having proximal and distal ends; a jaw unit carried by said distal end of said second shaft, said jaw unit comprising first and second jaw members with at least portions of said jaw members being electrically conductive;

means for causing one of said shafts to translate axially relative to the other of said shafts whereby said first shaft will act on said jaw members so as to cause said jaw members to close on one another when said translation is in a first axial direction; and means for connecting said electrically conductive portions of said jaw members to sources of electrical potential, whereby if different electrical potentials are applied to said jaw members an electrical current will flow between said jaw members to electrify a subject matter disposed between and engaged by said jaw members.

16. An instrument according to claim 15 wherein said jaw members are spring-biased to a normally open position.

17. A surgical instrument for conducting electrosurgery comprising:

a handle housing;

a first outer shaft and a second inner shaft having corresponding proximal and distal ends with said proximal ends being supported by said housing, with one of said shafts being movable axially relative to the other;

a jaw unit carried by one of said shafts, said jaw unit comprising at least first and second jaws with said jaws normally being deployed in spaced relation to one another in an open position;

manually operable means for causing relative axial movement of said shafts in a first axial direction or a second axial direction;

said outer shaft being disposed so as to extend over said jaws when said shafts undergo relative movement in said first axial direction, whereby when said shafts undergo relative movement in said first axial direction said outer shaft will cause said jaws to close towards one another; and means carried by said handle and extending along said second shaft for connecting said first and second jaws to different sources of electrical potential.

18. An instrument according to claim 17 wherein said last-mentioned means comprises first and second electrical leads disposed within said second shaft and connected to said first and second jaws.

19. An instrument according to claim 17 wherein said last-mentioned means comprises first and second electrical leads disposed within said second shaft and connected to said first and second jaws, and a bi-polar connector assembly attached to and projecting from said handle housing, said leads being connected to said connector assembly, whereby said jaws will be electrified with a potential difference between them when said connector assembly is coupled to a d.c. electrical power source.

20. An instrument according to claim 17 further including means electrically insulating said jaws from one another.

21. An instrument according to claim 20 wherein said jaws have proximal ends and distal ends, and further wherein said last-mentioned means comprises a mechanical member disposed between the proximal ends of said jaws.

22. An instrument according to claim 17 wherein said distal end of said inner shaft has a hollow extension, and said jaw unit comprises a pair of jaws each having a proximal end and a distal end, with said proximal ends extending into said hollow extension.

23. A surgical instrument comprising:

a hollow outer shaft having a longitudinal axis, a first proximal end and a first distal end;

an inner shaft coaxially disposed in said outer shaft with a space existing between said shafts, said inner shaft having a longitudinal axis, a second proximal end, and a second distal end, said shafts being disposed for relative axial movement;

means for surgical interaction with animal tissue attached to the distal end of said inner shaft, said surgical interaction means comprising first and second tissue interacting members movable relative to one another between a first open position and a second closed position by axially directed changes in the relative positions of said first and said second distal ends;

a handle mechanism coupled to said outer and inner shafts for effecting relative axial movement of said shafts and thereby changing the relative positions of said first and said second distal ends lengthwise of said longitudinal axis;

said handle mechanism comprising a first handle member affixed to the proximal end of said inner shaft, driver-responsive means attached to said outer shaft, a second handle member pivotally connected to said first handle member and movable relative to said first handle member between first and second operating positions, driver means carried by said second handle member engageable with said driver-responsive means for effecting reciprocal axial movement of said outer shaft relative to said inner shaft in response to movement of said first handle member between said first and second operating positions; and unidirectional locking means for locking said first and second handle members against relative movement in one predetermined direction; and means for introducing fluid to or removing fluid from said space.

24. An instrument according to claim 23 further characterized by at least one radially-extending opening in said outer shaft, and a collar assembly surrounding said outer shaft, said collar assembly having a chamber that communicates with said at least one radially-extending opening and a port that permits fluid to be introduced to or removed from said chamber.

25. A surgical instrument for conducting electrosurgery comprising:

a handle assembly;

an elongate dual shaft assembly having a proximal end retained within said handle assembly and a distal end to which is mounted a jaw assembly having at least two jaws that are movable relative to one another between open and closed positions, said shaft assembly comprising inner and outer shafts with one shaft movable axially relative to the other and said jaw assembly being arranged so that said jaws are urged to a closed position when said shafts undergo relative axial movement in a first direction, said handle assembly being operable to provide relative axial motion between said inner and outer shafts;

a ratchet device coupled between said dual shaft assembly and said handle assembly at the proximal end of said shaft assembly within said handle assembly, said ratchet device comprising a first member comprising a plurality of teeth, and a second member engageable with the teeth on said first member, said first and second members being movable relative to one another as the shafts undergo relative axial movement in response to operation of said handle assembly, the relative motion between said first and second members causing locking engagement and disengagement of said second member and said teeth, and said teeth and said second member being arranged so that when they are engaged the ratchet device will allow the shafts to undergo relative axial movement in said first direction but prevent the shafts from undergoing relative axial movement in a second opposite direction; and first and second means carried by said handle assembly for applying an electrical potential across said jaws.

26. A surgical instrument according to claim 25 further including selectively operable means for preventing engagement of said teeth and said second member, whereby said shafts are free to be moved axially relative to one another in said first or second directions by operation of said handle assembly.

27. A surgical instrument comprising:

a hollow outer shaft having a longitudinal axis, a first proximal end, and a first distal end;

an inner shaft coaxially disposed in said outer shaft, said inner shaft having a longitudinal axis, a second proximal end and a second distal end, said shafts being capable of relative reciprocal axial movement;

means for surgical interaction with animal tissue attached to the forward end of one of said shafts, said surgical interaction means comprising first and second tissue interacting members movable relative to one another between a first open position and a second closed position by axially directed changes in the relative positions of said first and said second distal ends; and a handle mechanism coupled to said outer and inner shafts for effecting relative axial movement of said shafts and thereby changing the relative positions of said first and said second distal ends lengthwise of said longitudinal axis;

said handle mechanism comprising a first handle member affixed to the proximal end of one of said shafts, driver-responsive means attached to the other of said shafts, a second handle member, means mounting said second handle member so that it is movable relative to said first handle member between first and second operating positions, driver means carried by said second handle member engageable with said driver-responsive means for effecting reciprocal axial movement of said other shaft relative to said one shaft in response to movement of said second handle member between said first and second operating positions;

ratchet means located within a housing for preventing relative axial movement of said shafts in one predetermined axial direction while permitting relative axial movement in a second opposite axial direction; and means carried by said handle mechanism for applying an electrical potential between said first and second tissue-interacting members.

28. An instrument according to claim 27 further including selectively operable means for disabling said ratchet means so as to free said other shaft for axial movement in said one predetermined axial direction.

* * * * *

UNITED STATES PATENT AND TRADEMARK OFFICE
CERTIFICATE OF CORRECTION

PATENT NO. : 5,611,813
DATED : March 18, 1997
INVENTOR(S) : Philip R. Lichtman

It is certified that error appears in the above-indentified patent and that said Letters Patent is hereby corrected as shown below:

Claim 4, column 18, line 45, after "when" and before "they", delete -- said --.

Signed and Sealed this

First Day of July, 1997

Attest:

BRUCE LEHMAN

Attesting Officer

Commissioner of Patents and Trademarks